United States Patent [19]

Wardell

[11] 4,152,448

[45] May 1, 1979

[54] METHOD AND COMPOSITION FOR THE TREATMENT OF A CONDITION OF THE GASTRO INTESTINAL TRACT

[75] Inventor: George Wardell, Loughborough, England

[73] Assignee: Fisons Limited, London, England

[21] Appl. No.: 755,606

[22] Filed: Dec. 29, 1976

Related U.S. Application Data

[63] Continuation of Ser. No. 471,139, May 17, 1974, abandoned, which is a continuation-in-part of Ser. No. 329,417, Feb. 5, 1973, abandoned.

[30] Foreign Application Priority Data

Feb. 15, 1972 [GB] United Kingdom ................. 6911/72
Feb. 2, 1974 [GB] United Kingdom ................. 4912/74

[51] Int. Cl.² .................................................. A61K 31/35
[52] U.S. Cl. ........................................................ 424/283
[58] Field of Search ........................................... 424/283

[56] References Cited

U.S. PATENT DOCUMENTS

| | | | |
|---|---|---|---|
| 3,686,412 | 8/1972 | Fitzmaurice et al. | 424/283 |
| 3,720,690 | 3/1973 | King et al. | 424/283 |
| 3,887,585 | 6/1975 | Kaminsky | 424/283 |

OTHER PUBLICATIONS

The Lancet, (1968), pp. 134–137.
The Lancet, (1970), pp. 893–895.
Nature, vol. 216, 12/30, 1967.
The Journal of Pediatrics, (1969), pp. 623–631, Freier et al.
The Lancet, (1973), pp. 913–915.

*Primary Examiner*—Frederick E. Waddell
*Attorney, Agent, or Firm*—Wenderoth, Lind & Ponack

[57] ABSTRACT

There is described a method of treatment of conditions of the gastro intestinal tract, in which conditions allergy or immune reactions play a contributory part, which method comprises per os administration of a compound of the formula I

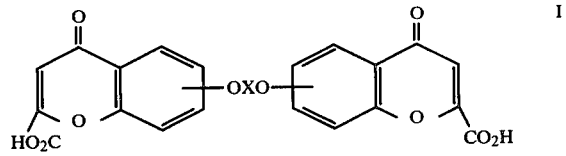

and therapeutically acceptable salts, esters and amides thereof, wherein X is a polymethylene chain containing 3 to 7 carbon atoms inclusive, which chain may be substituted by an —OH group, (as active ingredient), to a patient having such a condition.

18 Claims, No Drawings

METHOD AND COMPOSITION FOR THE TREATMENT OF A CONDITION OF THE GASTRO INTESTINAL TRACT

This application is a continuation of application Ser. No. 471,139, filed May 17, 1974 (now abandoned) which application is in turn a continuation-in-part of application Ser. No. 329,417, filed Feb. 5, 1973, now abandoned.

This invention relates to a new therapeutic method.

In U.S. Pat. No. 3,686,412 there are described a large number of bis-chromonyl compounds and their use in the treatment of asthma. These compounds are described as being administered orally, parenterally or more preferably by way of inhalation. These compounds are in general large and highly polar molecules and as such would not be expected to be absorbed through the gut to a sufficient extent to provide therapeutic levels of the compounds in the sub-epithelial tissues.

Surprisingly we have now found that a selected group of these compounds are useful in the treatment of conditions of the gastro intestinal tract in which allergy, immune or similar conditions play a contributory part.

According to the invention there is provided a method of treatment of conditions of the gastro intestinal tract, in which conditions allergy, immune or similar reactions play a contributory part, which method comprises per os administration of a compound of the formula I,

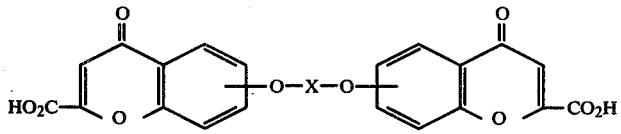

and therapeutically acceptable salts, alkyl C 1 to 10 esters, mono-alkyl C 1 to 10 amides, di-alkyl C 1 to 10 amides and unsubstituted amides thereof, wherein X is a polymethylene chain containing 3 to 7 carbon atoms inclusive, which chain may be substituted by an —OH group, (as active ingredient), to a patient having such a condition.

Suitable pharmaceutically acceptable salts include, for example, ammonium salts, alkali metal salts (e.g. sodium, potassium and lithium), alkaline earth metal salts (e.g. magnesium and calcium), and salts with organic amines (e.g. mono- di- or tri- alkyl C 1 to 6 amines, piperidine, and trialkanol C 1 to 6 amine salts). Esters which may be mentioned include simple alkyl esters (e.g. methyl, ethyl, propyl, isopropyl, butyl and tertiary butyl esters) and amides which may be mentioned include simple amides (for example amides with ammonia and lower alkylamines such as methylamine, ethylamine etc.).

Where the condition affects the rectum the administration may be by way of suppository, enema or other conventional vehicle for administration to the rectum. Where the condition effects another part of the gastro intestinal tract then the administration may be orally.

The drug may be administered as a conventional composition.

In order to produce suitable compositions the drug is worked up with inorganic or organic pharmaceutically acceptable adjuvants or excipients. Examples of such adjuvants are:

For tablets and dragees: Binders, for example, cellulosic materials, e.g. microcrystalline cellulose and methyl cellulose; disintegrating agents, for example starches, e.g. maize starch; stabilisers, e.g. against hydrolysis of the active ingredients; flavouring agents, for example sugars such as lactose; fillers; stearates and inorganic diluents, e.g. talc.

For syrups, suspensions or dispersions: A liquid vehicle in which the active ingredients may be dissolved or suspended, e.g. water; and suspending agents, e.g. cellulose derivatives, gums etc.

For hard or soft capsules: Diluents, e.g. lactose; glidants, e.g. stearates; inorganic materials, e.g. silica or talc; stabilisers and dispersing agents.

For suppositories: Natural or hardened oils, waxes etc. A large number of proprietary emulsifying bases are available and are suitable for use in suppositories. These include 'Witepsol' bases, consisting of hydrogenated triglycericles of lauric acid with added monoglycerides; and 'Massupol' bases, which consist of glyceryl esters of lauric acid with a very small amount of glyceryl monostearate.

For enemas: Water, sodium chloride, buffers etc.

The composition may also contain further adjuvants, for example a composition for use in tablets may contain lubricants and glidants to assist in tabletting, e.g. magnesium stearate, or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition may be formulated in sustained release form, e.g. by coating the drug particles themselves or granules thereof made with for example sucrose and of a size up to 2 mm in diameter with a layer of, e.g. beeswax, Carnauba wax, stearic or palmitic acids, cetyl alcohol or similar substances which could be expected to be slowly dissolved or digested or to act as semi-permeable membranes through which drug can diffuse when the preparations are ingested. The composition may contain drug particles or granules which are uncoated in admixture with particles or granules having one or more coats of the coating medium, and may be in the form of a capsule containing the particles or granules or alternatively a tablet, for which other adjuvants may be required, such as glidants or lubricants. The drug may be administered as an enteric coated composition to make the drug available at the appropriate part of the gastro-intestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

The drug may, if desired, be used in a specific form, e.g. having a substantial number of particles of effective particle size of less than 10 microns or particular crystal habit.

The drug may also be formulated as an aqueous, e.g. a water: chloroform (400:1), solution containing from 0.001 to 10.0% by weight of the drug. The free acids of formula I may conveniently be administered as an aqueous suspension containing from 0.1 to 10%, e.g. about 2% by weight of the drug.

The dosage to be administered will of course vary with the condition to be treated, with its severity and with its location. However in general a dosage of from about 20 to 1,000 preferably 100 to 750 and more preferably 200 to 500 mg of the drug administered 1 to 4 times a day (i.e. a daily dosage of 20 to 4,000 mg) is found to be satisfactory. We also provide a method in which the dosage is from 20 to 250 mg of the drug administered 2 to 4 times a day. The administration preferably takes place about 30 minutes before the patient takes food.

Conditions which may be treated by the method of our invention include Crohn's disease (a condition of the small, and sometimes also of the large intestine) atrophic gastritis (a condition of the stomach) ulcerative colitis (a condition of the large intestine and sometimes the small intestine) proctitis (a condition of the rectum and lower large intestine), coeliac disease (a condition of the small intestine), regional ileitis (a regional inflammatory condition of the terminal ileum), peptic ulceration (a condition of the stomach and duodenum), gastrointestinal allergy (e.g. milk, gluten and other food allergy), and irritable bowel syndrome. As a further condition there may be mentioned gastrointestinal bleeding induced by the administration of an anti-inflammatory, for example indomethacin or asprin.

Specific examples of the group X are groups of the formula —$(CH_2)_5$— and —$CH_2CHOHCH_2$—.

The chain —O—X—O— may link different or corresponding positions on the chromone nuclei.

Specific compounds which may be used in this invention are:

1,3-Bis(2-carboxychromon-5-yloxy)propane.
1,3-Bis(2-carboxychromon-5-yloxy)-2-hydroxypropane.
1,4-Bis(2-carboxychromon-5-yloxy)butane.
1,5-Bis(2-carboxychromon-5-yloxy)pentane.
1,6-Bis(2-carboxychromon-5-yloxy)hexane.
1,4-Bis(2-carboxychromon-5-yloxy)-2,3-dihydroxybutane.
1,4-Bis(2-carboxychromon-5-yloxy)-2-hydroxybutane.
1,5-Bis(2-carboxychromon-7-yloxy)-pentane.
1-(2-Carboxychromon-5-yloxy)-3-(2-carboxychromon-7-yloxy)-2-hydroxypropane.
1-(2-Carboxychromon-5-yloxy)-5-(2-carboxychromon-7-yloxy)pentane.
1,5-Bis(2-carboxychromon-8-yloxy)pentane.
1,5-Bis(2-carboxychromon-6-yloxy)pentane.
1,3-Bis(2-carboxychromone-7-yloxy)-2-hydroxypropane.
1,3-Bis(2-carboxychromon-6-yloxy)-2-hydroxypropane.
1-(2-Carboxychromon-5-yloxy)-3-(2-carboxychromon-6-yloxy)-2-hydroxypropane.
1-(2-Carboxychromon-5-yloxy)-3-(2-carboxychromon-8-yloxy)-2-hydroxypropane.

The above mentioned compounds may of course be used in the form of their pharmaceutically acceptable, e.g. their di-sodium, di-potassium, calcium, magnesium or di-piperidine salts. They may also be used in the form of their di-ethyl esters, or of their simple amides derived from ammonia. We prefer to use the compounds 1,3-bis(2-carboxy-chromon-5-yloxy)-2-hydroxypropane, or 1,3-bis(2-carboxy-chromon-7-yloxy)-2-hydroxypropane, or a pharmaceutically acceptable salt of either thereof.

The invention is illustrated, but in no way limited by the following Examples.

EXAMPLE 1

Four infants who were not tolerant to milk protein were given a solution of the di-sodium salt of 1,3-bis(2-carboxychromon-5-yloxy)-2-hydroxypropane (5 mls, 50 mg of the di-sodium salt) orally every 6 hours during their waking hours for a period of 7 days.

All four infants tolerated milk protein from the second to the seventh day of the treatment.

EXAMPLE 2

| Suppositories | | |
|---|---|---|
| (i) | Sodium Cromoglycate BP | 10g |
| | Theobroma Oil BP | to 100g |
| (ii) | Sodium Cromoglycate BP | 10g |
| | Emulsifying base | to 100g. |

Preparative method:

Melt the base over a water bath. Weight out the sodium cromoglycate, and place on a warmed slab. Add one half of the melted base and work quickly into a smooth cream. Stir into the remainder of the base to form a homogeneous mixture. Allow to cool with stirring until the mixture is just pourable, then pour into suitable lubricated suppository moulds. Cool and trim with a sharp knife.

| (iii) | Sodium Cromoglycate BP | 10g |
|---|---|---|
| | Gelatin BP | 15g |
| | Glycerin BP | 50g |
| | Purified water BP | to 100g. |

Heat the glycerin to boiling and dissolve the sodium cromoglycate in the glycerin with the aid of a little purified water. Dissolve the gelatin in the minimum amount of hot water with stirring. Mix the two hot solutions, add hot water to 100 g, and stir whilst cooling. When the mixture is just pourable, pour into lubricated moulds. Cool and trim with a sharp knife.

| (iv) | Sodium Cromoglycate | 10% |
|---|---|---|
| | Polyethylene glycol 400 | 15% |
| | Polyethylene glycol 1500 | 30% |
| | Polyethylene glycol 6000 | 30% |
| | Purified water | to 100% |

Heat the polyethylene glycol 400° to 90° C., add the Sodium Cromoglycate and dissolve with the aid of the minimum quantity of hot water. Melt the PEG 6000 and PEG 1500 together, and mix the two hot mixtures. Allow to cool with stirring until the mixture is just pourable, pour into lubricated moulds. Cool and trim with a sharp knife.

EXAMPLE 3

| Enema | |
|---|---|
| Sodium Cromoglycate BP | 0.50g |
| Sodium Chloride BP | 0.44g |
| Sodium Phosphate BP | 1.91g |
| Sodium Acid Phosphate BP | 0.21g |
| Purified Water BP | to 100 ml. |

Methyl cellulose or other agents may be added to aid retention of the solution in the bowel.

I claim:

1. A method of treatment of a condition of the gastro-intestinal tract selected from the group consisting of Crohn's disease, atrophic gastritis, ulcerative colites, proctitis, coeliac disease, regional ileitis, peptic ulceration, irritable bowel syndrome and gastro-intestinal bleeding induced by the administration of an anti-inflammatory, which method comprises per os administration of a daily dosage of from 20 to 4,000 mg. of a member selected from the group consisting of a compound of the formula

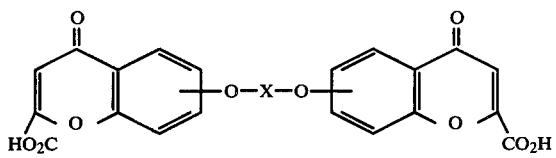

a therapeutically acceptable salt, an alkyl C 1 to 10 ester, a mono-alkyl C 1 to 10 amide, a di-alkyl C 1 to 10 amide and an unsubstituted amide thereof, wherein X is a polymethylene chain containing 3 to 7 carbon atoms inclusive, which chain may be substituted by an —OH group, to a patient having such a condition.

2. A method according to claim 1 wherein the compound is 1,3-bis(2-carboxy-chromon-5-yloxy)-2-hydroxypropane or a pharmaceutically acceptable salt thereof.

3. A method according to claim 1 wherein the compound is 1,3-bis(2-carboxy-chromon-7-yloxy)-2-hydroxypropane or a pharmaceutically acceptable salt thereof.

4. A method according to claim 1 wherein the pharmaceutically acceptable salt is an ammonium, alkali metal or alkaline earth metal salt.

5. A method according to claim 1, wherein the patient receives unit dosages of from 20 to 1000 mg. of the active ingredient.

6. A method according to claim 5 wherein the unit doses are from 100 to 750 mg. of active ingredient.

7. A method according to claim 5, wherein the unit doses are from 200 to 500 mg. of active ingredient.

8. A method according to claim 1 in which the patient receives from 20 to 250 mg. of the active ingredient 2 to 4 times a day.

9. A method according to claim 1 wherein the condition treated is Crohn's disease.

10. A method according to claim 1 wherein the condition treated is atrophic gastritis.

11. A method according to claim 1 wherein the condition treated is ulcerative colitis.

12. A method according to claim 1 wherein the condition treated is proctitis.

13. A method according to claim 1 wherein the condition treated is coeliac disease.

14. A method according to claim 1 wherein the condition treated is regional ileitis.

15. A method according to claim 1 wherein the condition treated is peptic ulceration.

16. A method according to claim 1 wherein the condition treated is irritable bowel syndrome.

17. A method according to claim 1 wherein the condition treated is gastrointestinal bleeding induced by the administration of an anti-inflammatory.

18. A method for the treatment of a condition of the gastro-intestinal tract selected from the group consisting of Crohn's disease, ulcerative colitis, proctitis, irritable bowel syndrome and gastro-intestinal bleeding induced by the administration of an anti-inflammatory, which method comprises administering to the gastro-intestinal tract of a patient suffering from said condition a daily dosage of from 20 to 4,000 mg. of a member selected from the group consisting of a compound of the formula

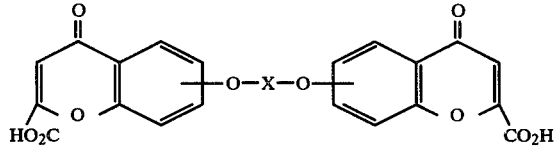

a therapeutically acceptable salt, an alkyl C 1 to 10 ester, a mono-alkyl C 1 to 10 amide, a di-alkyl C 1 to 10 amide and an unsubstituted amide thereof, wherein X is a polymethylene chain containing 3 to 7 carbon atoms inclusive, which chain may be substituted by an —OH group.

* * * * *